(12) United States Patent (10) Patent No.: US 8,282,590 B2
Goswami et al. (45) Date of Patent: Oct. 9, 2012

(54) TOE BRACE DESIGNS

(75) Inventors: Tarun K. Goswami, Beavercreek, OH (US); Allison L. Van Horn, Centerville, OH (US); Alexander O. Sheets, Dayton, OH (US)

(73) Assignee: Wright State University, Dayton, OH (US)

( * ) Notice: Subject to any disclaimer, the term of this patent is extended or adjusted under 35 U.S.C. 154(b) by 278 days.

(21) Appl. No.: 12/748,404

(22) Filed: Mar. 27, 2010

(65) Prior Publication Data

US 2010/0249687 A1 Sep. 30, 2010

Related U.S. Application Data

(60) Provisional application No. 61/163,911, filed on Mar. 27, 2009.

(51) Int. Cl.
*A61F 5/00* (2006.01)
(52) U.S. Cl. .......................................... 602/23; 602/30
(58) Field of Classification Search .......... 602/5, 30–31, 602/23; 128/892–894
See application file for complete search history.

(56) References Cited

U.S. PATENT DOCUMENTS

| 4,940,046 | A | * | 7/1990 | Jacoby | 602/30 |
| 5,453,083 | A | * | 9/1995 | Kasahara | 602/30 |
| 5,928,173 | A |   | 7/1999 | Unruh | |
| 6,093,163 | A | * | 7/2000 | Chong et al. | 602/30 |

OTHER PUBLICATIONS

"Wear rate model for UHMWPE in total joint applications," Alhassan et al., WEAR, vol. 265, 8-13 (Nov. 5, 2007).
"Decision making in the treatment of hallux valgus," Joseph et al., Bull NYU Hosp Jr. Dis. 65(1): 19-23 (2007).
The Pathogenesis and biomechanics of turf toe, Childs, S.G., Orthop Nurse. 25(4): 276-80 (Jul./Aug. 2006).
Who's afraid of the big bad Wolff?: 'Wolff's law' and bone functional adaptation, Ruff et al., Am JPhys Anthropol. 129: 484-98 (Ja. 19, 2006).
"Daily high heal use and injury prevention in women," Arias, PED 763: Biomechanics (Fall 2005).
"First metatarsophalangeal joint reaction forces during high-heel gait," McBride et al., Foot & Ankle. 11(5): 282-8 (Apr. 1991).

* cited by examiner

*Primary Examiner* — Michael A. Brown
(74) *Attorney, Agent, or Firm* — Dinsmore & Shohl, LLP

(57) ABSTRACT

In various embodiments, provided are braces for use in supporting the metatarsophalangeal joint, reducing or maintaining the intermetatarsal angle, enhancing or maintaining alignment of the hallux, or combinations thereof in a subject having hallux valgus.

20 Claims, 17 Drawing Sheets

TOE BRACE DESIGNS

CROSS REFERENCE TO RELATED APPLICATION

This application claims priority to and any other benefit of U.S. Provisional Patent Application Ser. No. 61/163,911, filed Mar. 27, 2009, the entirety of which is incorporated by reference herein.

BACKGROUND

Hallux valgus is characterized as a deformity of the great toe (hallux) and first metatarsophalangeal joint, wherein the first metatarsal is medially deviated, the great toe is laterally deviated and/or rotated on the head of the metatarsal, the plantar pad and sesamoids are displaced with the toe, and the ligaments on the medial side of the metatarsophalangeal joint are stretched. The position of the great toe with respect to the second toe can be overriding, underriding, abutting, or without contact. Thus, hallux valgus can involve transverse plane deformities (hallux abductus), or frontal and transverse plane deformities (hallux abductovalgus). With respect to deformities in the transverse plane, the angle between the longitudinal axis of the metatarsals of the first and second toes (intermetatarsal angle) typically deviates beyond the normal range of 8-12°. With respect to deformities in the frontal plane, the angle between the longitudinal axis of the metatarsal and proximal phalanx of the great toe (hallux valgus angle) typically deviates beyond the normal upper limit of 15-20°.

In addition to physical deformity, hallux valgus is often accompanied by formation of a callous, bursa, or bunion over the first metatarsal head, pain in the first metatarsophalangeal joint during ambulation, pain in the metatarsal head, and combinations thereof.

Hallux valgus is estimated to affect more than 43 million people in the United States, with incidence more predominate in females, those older than 60 years of age, teenagers who wear high heels, and athletes. It can develop due to numerous factors, including biomechanical instability (e.g., excessive protonation), arthritic/metabolic conditions (e.g., osteo/rheumatoid arthritis), neuromuscular disease (e.g., multiple sclerosis), trauma (e.g., soft-tissue sprains, dislocations, and sports-related injuries), and structural deformities (e.g., abnormal metatarsal length). Additionally, there tends to be familial disposition to developing hallux valgus.

Development of hallux valgus typically occurs in four stages. See Root, ML, "Normal and Abnormal Function of the Foot," Vol. 2, *Clinical Biomechanics* (1977). The first stage is associated with lateral subluxation (partial or complete dislocation) of the proximal phalanx. The second stage is associated with increased abduction of the hallux in the transverse and/or frontal planes. The third stage is associated with additional subluxation at the first metatarsophalangeal joint. The fourth stage is associated with dislocation of the first metatarsophalangeal joint.

Hallux valgus is a complex deformity and various approaches to treating or correcting the deformity may be available. For example, surgery is the only means of correcting the deformity and when hallux valgus is in its later stages, surgery may be the only means of treatment. However, when hallux valgus is in its early stages, or where surgical correction is contraindicated, braces, straps, splints, orthotics, or combinations thereof may be used to manage progression of the deformity and relieve the associated symptoms.

Because braces, straps, splints, and orthotics are non-invasive, cost-effective, and may be self-applied, they represent important means of treating hallux valgus. Such devices are typically designed to relieve the symptoms of the deformity by attempting to reduce the intermetatarsal angle, realign the hallux to a rectus (rather than an abductus) position, or combinations thereof by applying force to various portions of the foot. Braces, straps, splints, and orthotics may also be used for post-operative wear to maintain appropriate alignment during the healing process, to prevent recurrence, or both.

Conventional non-surgical treatment devices have numerous disadvantages, including bulkiness, difficulty in wearing in shoes, requiring periodic readjustment, creation of undesired pressure and irritation, complexity of application, and failure to relieve the deformity. Accordingly, there is need in the art for improved non-surgical devices for use in treating hallux valgus.

SUMMARY

Embodiments of the present invention provide braces for use in supporting the metatarsophalangeal joint, reducing or maintaining the intermetatarsal angle, enhancing or maintaining alignment of the hallux, or combinations thereof in a subject having hallux valgus.

In various embodiments, provided are braces for treating hallux valgus, comprising a distal portion comprising a cavity adapted to receive at least a portion of the hallux; a proximal portion comprising a cavity adapted to receive at least a portion of the midfoot and hallux; and one or more stabilization members.

In various embodiments, provided are braces for treating hallux valgus, comprising a first member comprising opposing longitudinal edges, each edge having one or more locking members; a second member comprising opposing longitudinal edges, each edge having one or more cavities adapted to receive the one or more locking members; wherein the one or more locking members and one or more cavities are adapted to reversibly lock the first member to the second member; and wherein the reversibly locked first member and second member define a cavity adapted to receive at least a portion of the hallux.

In various embodiments, also provided are methods of treating hallux valgus comprising applying one or more of the provided braces to the foot of a subject.

These and additional features of the invention will become apparent in the course of the following detailed description.

BRIEF DESCRIPTION OF THE DRAWINGS

A more complete appreciation of the invention and the many embodiments thereof will be readily obtained as the same becomes better understood by reference to the following detailed description when considered in connection with the accompanying drawings, wherein.

DETAILED DESCRIPTION

Figure 1:
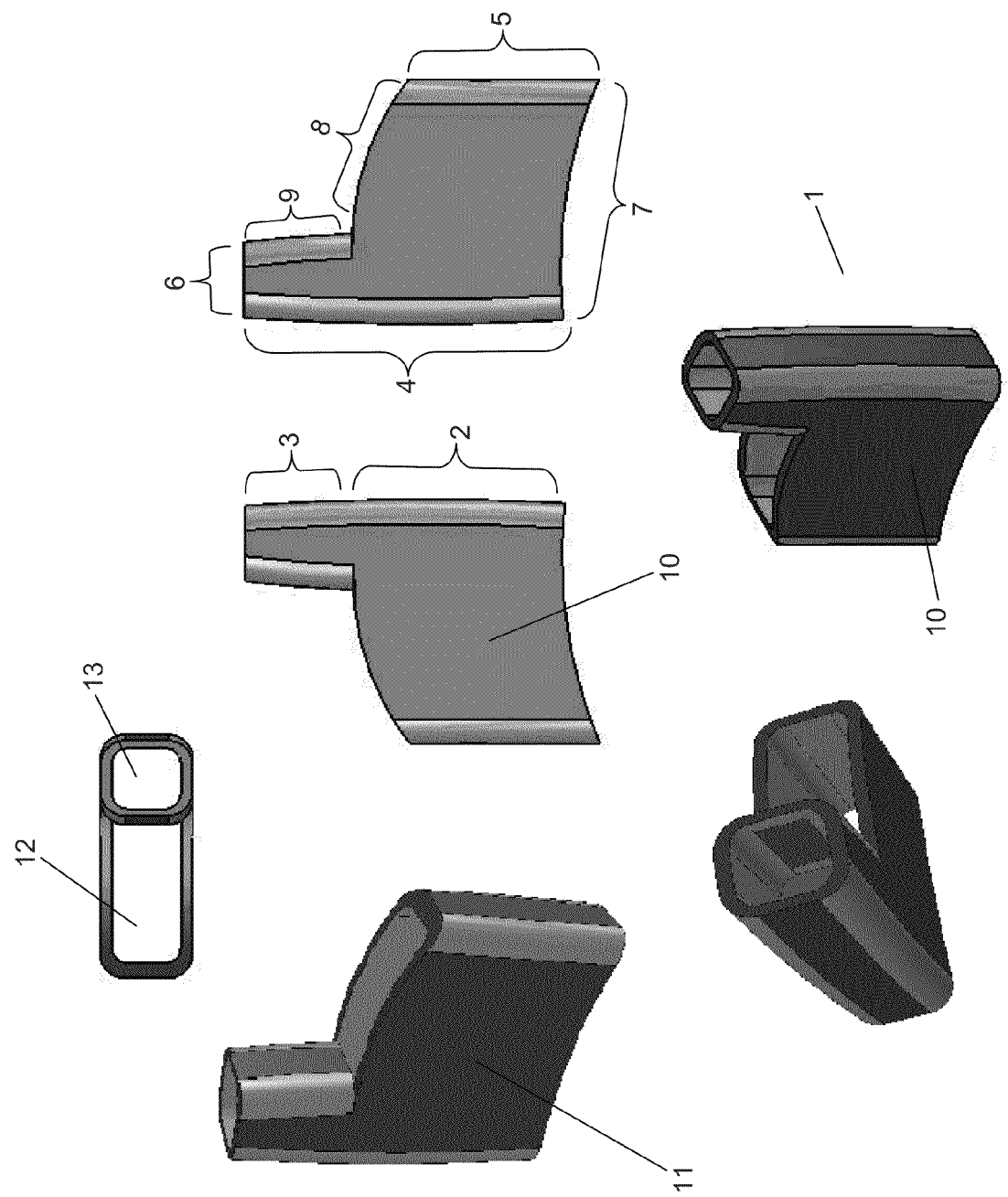
FIG. 1-2 illustrate two examples of braces and elements thereof.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art. Similarly, the present invention should not be considered limited to the specific examples described herein, but rather should be understood to cover all aspects of the invention. Various modifications and equivalents, as well as numerous structures and devices to which the present invention may be applicable will be readily apparent to those of skill in the art. Those skilled in the art will understand that various changes may be made without departing from the scope of the invention, which is not to be considered limited to what is described in the specification.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

In various embodiments, braces for treating hallux valgus in the foot of a subject are provided, comprising a distal portion comprising a cavity adapted to receive at least a portion of the hallux of the foot; a proximal portion comprising a cavity adapted to receive at least a portion of the midfoot and hallux of the foot; and one or more stabilization members adapted to provide one or more of rigidity, resiliency, or cushioning to at least a part of the distal portion, at least a part of the proximal portion, or combinations thereof.

Figure 2:
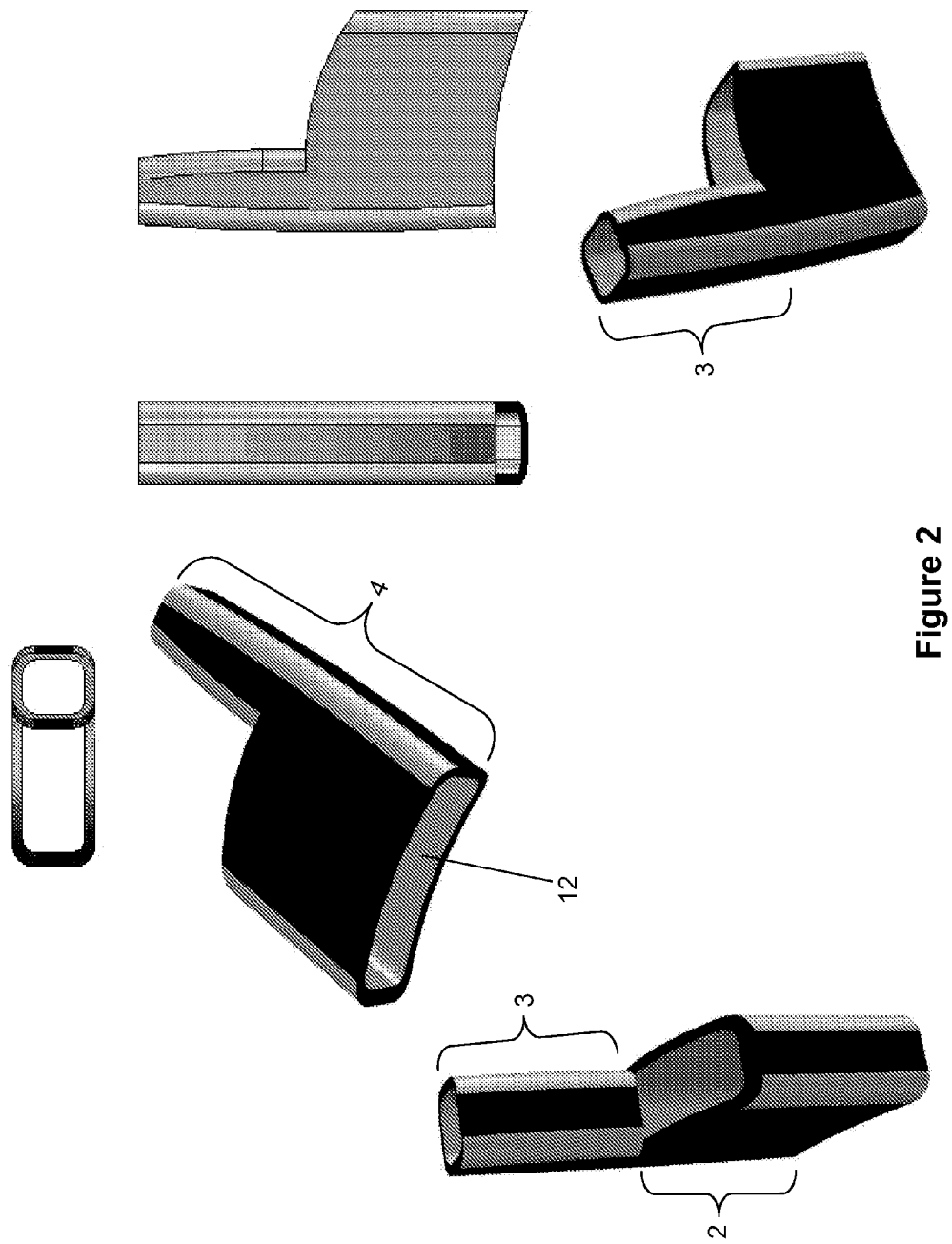

Referring to FIGS. 1-2, illustrated are embodiments of provided braces. As illustrated, a brace 1 comprises a proximal portion 2 and a distal portion 3. In some embodiments, and as shown, the proximal 2 and distal 3 portions are of unitary construction. However, it is also contemplated that the proximal 2 and distal 3 portions may be individual portions that are worn together and cooperate to function as one device or that are mechanically joined to become one device. The brace 1 further comprises a medial face 4, a lateral face 5, a distal face 6, a proximal face 7, an intermediate face 8, an inter-phalangeal face 9, a ventral face 10 (shown for brace of left foot) and a dorsal face 11 (shown for brace of left foot)

The medial face 4 comprises portions of the proximal portion 2 and the distal portion 3 and is designed to span the length of at least a portion of the metatarsal and proximal phalanx bones of the hallux, and provide stabilization to the metatarsophalangeal joint. In some embodiments, the medial face 4 spans the length of all of the metatarsal and proximal phalanx bones in the foot. In some embodiments, it spans the length of all of the metatarsal and proximal phalanx bones and at least a portion of the distal phalanx bone. In some embodiments, the medial face 4 has a shape selected from rhombus, rhomboid, rectangle, square, oblong, oval, or variations thereof. As shown, the medial face 4 is a rounded rectangle. Additionally, the medial face 4 may be planar or non-planar.

In some embodiments, the medial face 4 comprises a stabilization member (not shown). The stabilization member may be any material that provides sufficient rigidity, resiliency, cushioning, or combinations thereof to at least a portion of the medial face 4 to reduce or maintain the hallux valgus angle when the brace 1 is worn. In some embodiments, the stabilization member spans the entire length, a portion of the length, the entire width, a portion of the width, or combinations thereof of the medial face 4. In some embodiments, the stabilization member may span from 0-100% of the area of the medial face 4. Accordingly, the stabilization member may span from 0-10%, 10-20%, 20-30%, 30-40%, 40-50%, 50-60%, 60-70%, 70-80%, 80-90%, 90-100% of the area of the medial face 4. In some embodiments, the stabilization member may be exterior-oriented, interior-oriented, or integral with the medial face 4. For example, the stabilization member may be formed as woven fibers, stitching, a panel, a pad, a rod, a rib, an insert, or other suitable material. In some embodiments, the stabilization member comprises a material selected from natural fibers, synthetic fibers (including but not limited to carbon fibers and polychloroprene rubber such as for example Neoprene™), polymeric materials [including but not limited to ultra-high molecular weight polyethylene, polypropylene, polyetheretherketone ("PEEK"), and fluorocarbon polymers such as, for example, Teflon®], hydrogels [including but not limited to poly(hydroxyethyl methacrylic acid) ("HEMA") and silicone hydrogels], and combinations thereof.

The lateral face 5 is designed to span the length of at least a portion of the metatarsal bone of the fifth toe. In some embodiments, it spans at least a portion of the length of the metatarsal bone and at least a portion of the length of the proximal phalanx bone. In some embodiments, it spans at least a portion of the length of the metatarsal bone, all of the length of the proximal phalanx bone, and at least a portion of the length of the middle phalanx bone. In some embodiments, the lateral face 5 has a shape selected from rhombus, rhomboid, rectangle, square, oblong, oval, or variations thereof. As shown, the lateral face 5 is a rounded rectangle. Additionally, the lateral face 5 may be planar or non-planar.

The distal face 6 is designed to span the circumference of the hallux at or proximate to either the proximal phalanx or distal phalanx bones. In some embodiments, the distal face 6 has a shape selected from rhombus, rhomboid, rectangle, square, oblong, oval, circular, or variations thereof. As shown, the distal face 6 is a rounded square. Additionally, the distal face 6 may be planar or non-planar.

The proximal face 7 is designed to span the circumference of the midfoot at or proximate to the proximal end of the metatarsals. In some embodiments, the proximal face 7 has a shape selected from rhombus, rhomboid, rectangle, square, oblong, oval, or variations thereof. Additionally, the proximal face 7 may be planar or non-planar. As shown, the proximal face 7 has a shape that is a non-planar rounded rectangle. The shape shown is allows the brace 1 to align with the natural contour of the midfoot.

The intermediate face 8 is formed between the lateral face 5 and the inter-phalangeal face 9 of the brace 1 and is designed to span the circumference of the midfoot at or proximate to the distal end of the second through fifth metatarsals. In some embodiments, the intermediate face 8 has a shape selected from rhombus, rhomboid, rectangle, square, oblong, oval, or variations thereof. Additionally, the intermediate face 8 may be planar or non-planar. As shown, the intermediate face 8 has a shape that is a non-planar rounded rectangle. The shape shown is intended to allow the brace 1 to align with the natural contour of the midfoot.

The inter-phalangeal face 9 is formed between the intermediate face 8 and the distal face 6 and is designed to span the length of at least a portion of the hallux at or proximate to the proximal phalanx bone. In some embodiments, the inter-phalangeal face 9 also spans at least a portion of the length of the metatarsal bone. In some embodiments, the inter-phalangeal face 9 also spans at least a portion of the length of the distal phalanx bone. In some embodiments, the shape of the inter-phalangeal face 9 is selected from rhombus, rhomboid, rectangle, square, oblong, oval, or variations thereof. As shown, the inter-phalangeal face 9 is a rounded rectangle. Additionally, the inter-phalangeal face 9 may be planar or non-planar.

In some embodiments, the inter-phalangeal face 9 provides stabilization to the metatarsophalangeal joint, the proximal phalanx, or both. In some embodiments, stabilization is provided by a stabilization member (not shown). The stabilization member may be any material that provides sufficient rigidity, resiliency, cushioning, or combinations thereof to at least a portion of the inter-phalangeal face 9 to reduce or maintain the hallux valgus angle when the brace 1 is worn. In some embodiments, the stabilization member spans the entire length, a portion of the length, the entire width, a portion of the width, or combinations thereof of the inter-phalangeal face 9. In some embodiments, the stabilization member may span from 0-100% of the area of the inter-phalangeal face 9. Accordingly, the stabilization member may span from 0-10%, 10-20%, 20-30%, 30-40%, 40-50%, 50-60%, 60-70%, 70-80%, 80-90%, 90-100% of the area of the inter-phalangeal face 9. In some embodiments, the stabilization member may be exterior-oriented, interior-oriented, or integral with the inter-phalangeal face 9. For example, the stabilization member may be formed as woven fibers, stitching, a panel, a pad, a rod, a rib, an insert, or other suitable materials. In some embodiments, the stabilization member comprises a material selected from natural fibers, synthetic fibers (including but not limited to carbon fibers and polychloroprene rubber such as for example Neoprene™), polymeric materials [including but not limited to ultra-high molecular weight polyethylene, polypropylene, polyetheretherketone ("PEEK"), and fluorocarbon polymers such as, for example, Teflon®], hydrogels [including but not limited to poly(hydroxyethyl methacrylic acid) ("HEMA") and silicone hydrogels], and combinations thereof.

The ventral face 10 is designed to span the ventral side of the midfoot and hallux and is bounded by the medial face 4, the lateral face 5, the distal face 6, the proximal face 7, the intermediate face 8, and the inter-phalangeal face 9.

The dorsal face 11 is designed to span the dorsal side of the midfoot and hallux and is bounded by the medial face 4, the lateral face 5, the distal face 6, the proximal face 7, the intermediate face 8, and the inter-phalangeal face 9.

Collectively, the lateral face 5, proximal face 7, intermediate face 8, and at least portions of the ventral 10, dorsal 11, and medial 4 faces define a proximal cavity 12 for receiving at least a portion of the midfoot and hallux. Moreover, the proximal cavity 12, lateral face 5, proximal face 7, intermediate face 8, and at least portions of the ventral 10, dorsal 11, and medial 4 faces define the proximal portion 2. Collectively, the distal face 6, inter-phalangeal face 9, and at least portions of the ventral 10, dorsal 11, and medial 4 faces define a distal cavity 13 for receiving at least a portion of the hallux. Moreover, the distal cavity 13, distal face 6, inter-phalangeal face 9, and at least portions of the ventral 10, dorsal 11, and medial 4 faces define the distal portion 3.

In some embodiments, and as illustrated in FIG. 1, the distal portion 3 is adapted to encapsulate at least a portion of the hallux and span the length of at least a portion of the proximal phalanx bone. In some embodiments, the distal portion 3 also spans at least a portion of the length of the metatarsal bone. In alternative embodiments, and as illustrated in FIG. 2, the distal portion 3 is adapted to encapsulate at least a portion of the hallux and span the length of at least a portion of the metatarsophalangeal joint, all of the length of the proximal phalanx bone, and at least a portion of the length of the distal phalanx bone. In some embodiments, the distal portion 3 also spans at least a portion of the length of the metatarsal bone.

Collectively, the proximal portion 2, distal portion 3, or combination thereof is designed to relieve the symptoms of the deformity by supporting the metatarsophalangeal joint, reducing or maintaining the intermetatarsal angle, enhancing or maintaining alignment of the hallux, or combinations thereof. In some embodiments, one or more stabilizing members may be used in the brace 1 to provide a desired benefit.

In some embodiments, braces may be selected from small, medium, or large sizes as necessary to approximate the anatomy of the subject. In some embodiments, braces may comprise one or more dimensions set forth in Table 1. In some embodiments, braces may be gender specific and comprise one or more dimensions set forth in Table 2. In some embodiments, a brace may be customized to the anatomy of the subject.

TABLE 1

| Location | Dimension (cm) |
|---|---|
| Foot Circumference at Metatarsophalangeal Joints | 19-26 |
| Great Toe/Hallux Circumference | 6-12 |
| Digits 2-5 Width | 6-11 |
| Foot Width at Metatarsophalangeal Joints | 7.5-12.5 |
| Tip of First Digit to Midfoot | 12-19 |
| Base of Fifth Digit to Midfoot | 5-10 |

TABLE 2

| Location | Dimension (cm) Female | Dimension (cm) Male |
|---|---|---|
| Foot Circumference at Metatarsophalangeal Joints | 19-23 | 22-26 |
| Great Toe/Hallux Circumference | 6-10 | 8-12 |
| Digits 2-5 Width | 6-10 | 7-11 |
| Foot Width at Metatarsophalangeal Joints | 7.5-11.5 | 8.5-12.5 |
| Tip of First Digit to Midfoot | 12-16 | 15-19 |
| Base of Fifth Digit to Midfoot | 5-9 | 6-10 |

The provided braces may be comprised of any material suitable for use with wearable braces. For example, it is contemplated that the material of construction may be selected from rubber, synthetic rubber (including but not limited to polychloroprene rubber), natural fibers, synthetic fibers (including but not limited to carbon fibers), polymeric materials (including but not limited to fluorocarbon polymers such as, for example, Teflon® polyethylene, polypropylene, PEEK), hydrogels (including but not limited to polyHEMA and silicone hydrogels), and combinations thereof. In some embodiments, braces may be partially or completely constructed of a thin elastomeric material. One example of a suitable elastomeric material is polychloroprene rubber such as, for example, Neoprene™. In some embodiments, braces may be substantially constructed of an elastomeric material and comprise one or more hydrogel stabilization members. In some embodiments, the hydrogel members are provided in the form of are pads, cushions, panels, or inserts. In some embodiments, braces may be substantially constructed of an elastomeric material and comprise one or more ultra-high molecular weight polyethylene panels. In some embodiments, braces may be substantially constructed of an elastomeric material and comprise one or more polyfluorocarbon stabilization members. In some embodiments, the polyfluorocarbons, preferably in the form of fibers, are woven into one or more portions of the brace. For example, the polyfluorocarbon may be stitching, a panel of polyfluorocarbon, or a seam. In some embodiments, braces may be substantially constructed of an elastomeric material and comprise one or more carbon fiber stabilization members. In some embodiments, the carbon fibers are woven into one or more portions of the brace. For example, the carbon fibers may be stitching, a panel of carbon fibers, or a seam.

Figure 3:
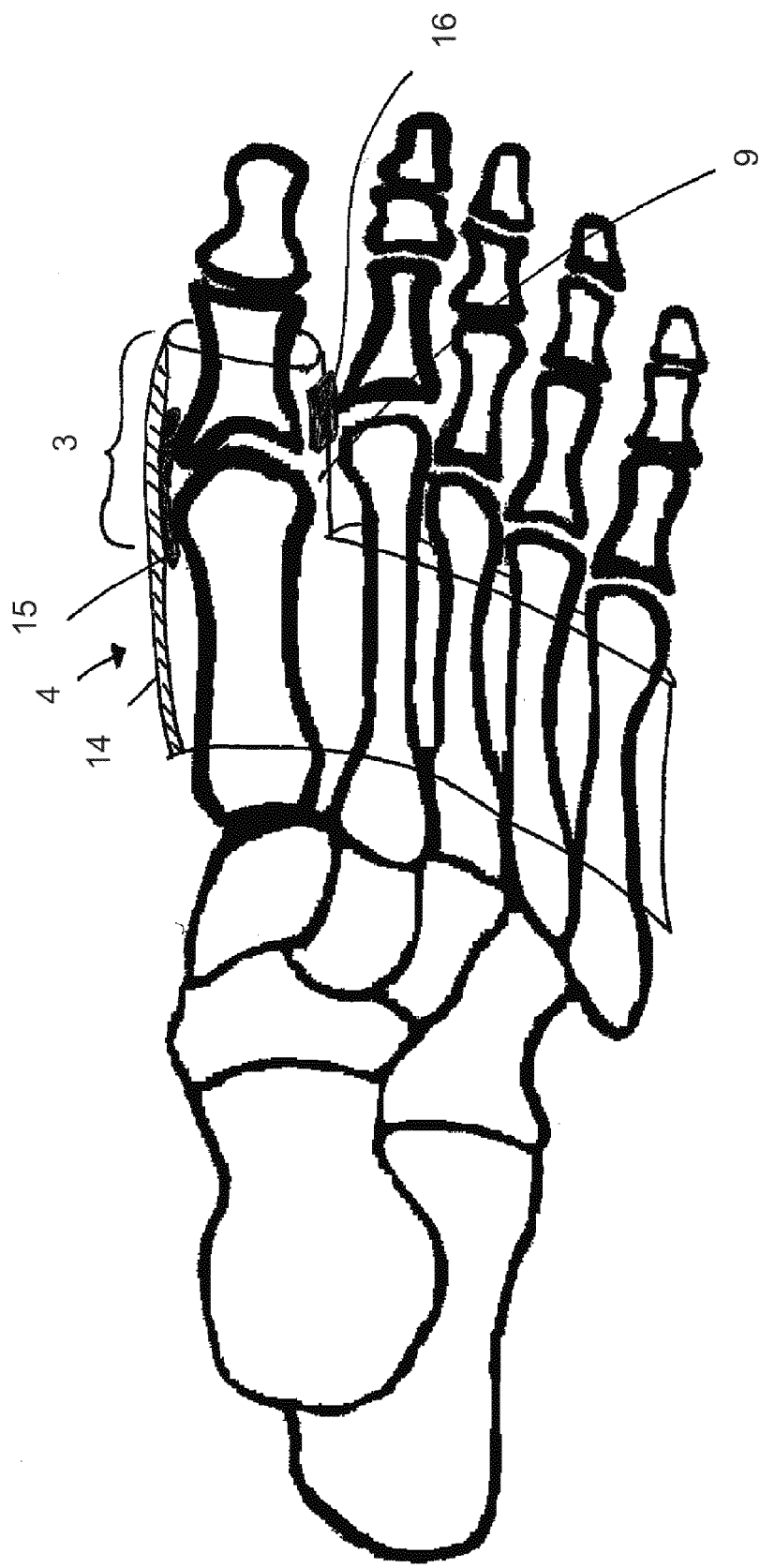
FIG. 3 illustrates one example of a brace as worn, and certain elements thereof; wherein the stabilization members of the exemplary brace are illustrated.

Referring to FIG. 3, one embodiment of a brace is illustrated wherein the distal portion 3 is adapted to encapsulate and span the length of a portion of the metatarsal bone, the entire metatarsophalangeal joint, and a portion of the proximal phalanx bone. As shown, the medial face 4 comprises a primary medial stabilization member 14 spanning the entire length of the medial face 4; and a secondary medial stabilization member 15 spanning the length of a portion of the metatarsal bone, the entire metatarsophalangeal joint, and a portion of the proximal phalanx bone. As shown, the inter-phalangeal face 9 comprises a secondary inter-phalangeal stabilization member 16. In some embodiments, the stabilization members 14, 15, 16 have sufficient rigidity, resiliency, cushioning, or combinations thereof to support the metatarsophalangeal joint, reduce or maintain the intermetatarsal angle, enhance or maintain alignment of the hallux, or combinations thereof. In some embodiments, the primary medial stabilization member 14 is woven into the medial face 4. In some embodiments, the primary medial stabilization member 14 is polyfluorocarbon fibers woven into the medial face 4. In some embodiments, the primary medial stabilization member 14 is carbon fibers woven into the medial face 4. In some embodiments, the secondary medial stabilization member 15 is an interior-oriented pad or insert. In some embodiments, the secondary medial stabilization member 15 is a hydrogel. In some embodiments, the secondary inter-phalangeal stabilization member 16 is an interior-oriented pad or insert. In some embodiments, the secondary inter-phalangeal stabilization member 16 is an exterior-oriented pad or cushion. In some embodiments, the secondary inter-phalangeal stabilization member 16 is a hydrogel.

In some embodiments, wherein the primary medial stabilization member 14 is comprised of a polyfluorocarbon and the secondary medial stabilization member 15 is a hydrogel, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein the primary medial stabilization member 14 is carbon fibers and the secondary medial stabilization member 15 is a hydrogel, the brace is used to support the metatarsophalangeal joint, reduce or maintain the intermetatarsal angle, enhance or maintain alignment of the hallux, or combinations thereof in a subject having minor to severe hallux valgus.

Figure 4:
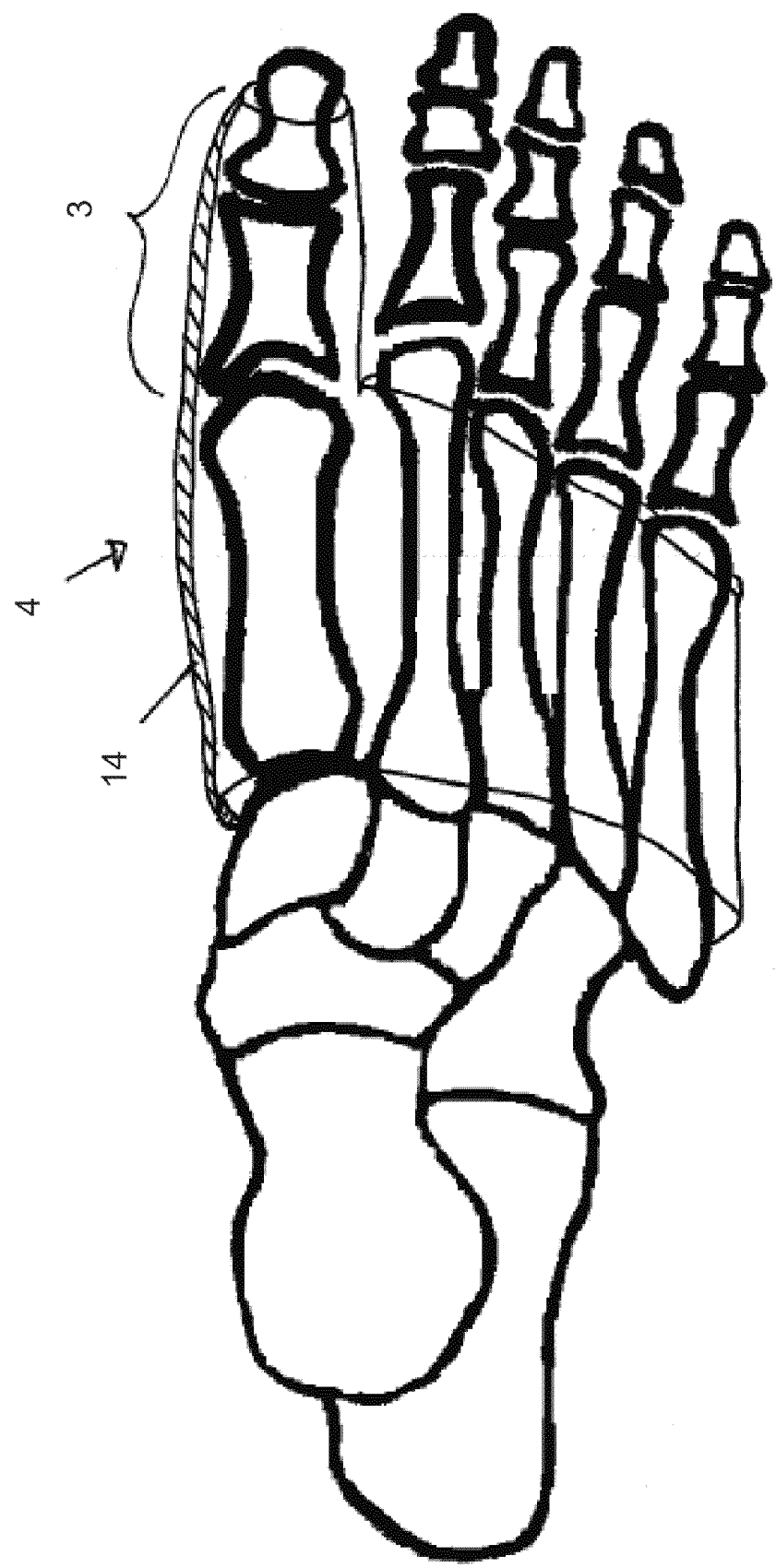
FIG. 4 illustrates another example of a brace as worn, and certain elements thereof; wherein the stabilization members of the exemplary brace are illustrated.

Referring to FIG. 4, one embodiment of a brace is illustrated wherein the distal portion 3 is adapted to encapsulate and span the length of a portion of the metatarsophalangeal joint, the entire proximal phalanx bone, and a portion of the distal phalanx bone. As shown, the medial face 4 comprises a primary medial stabilization member 14 spanning the entire length of the medial face 4. In some embodiments, the stabilization member 14 has sufficient rigidity, resiliency, cushioning, or combinations thereof to support the metatarsophalangeal joint, reduce or maintain the intermetatarsal angle, enhance or maintain alignment of the hallux, or combinations thereof. In some embodiments, the stabilization member 14 is woven into the medial face 4. In some embodiments, the stabilization member 14 is polyfluorocarbon fibers woven into the medial face 4. In some embodiments, the stabilization member 14 is carbon fibers woven into the medial face 4.

In some embodiments, wherein the primary medial stabilization member 14 is a polyfluorocarbon, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein the primary medial stabilization member 14 is carbon fibers, the brace is used to support the metatarsophalangeal joint, reduce or maintain the intermetatarsal angle, enhance or maintain alignment of the hallux, or combinations thereof in a subject having minor to severe hallux valgus.

Figure 5:
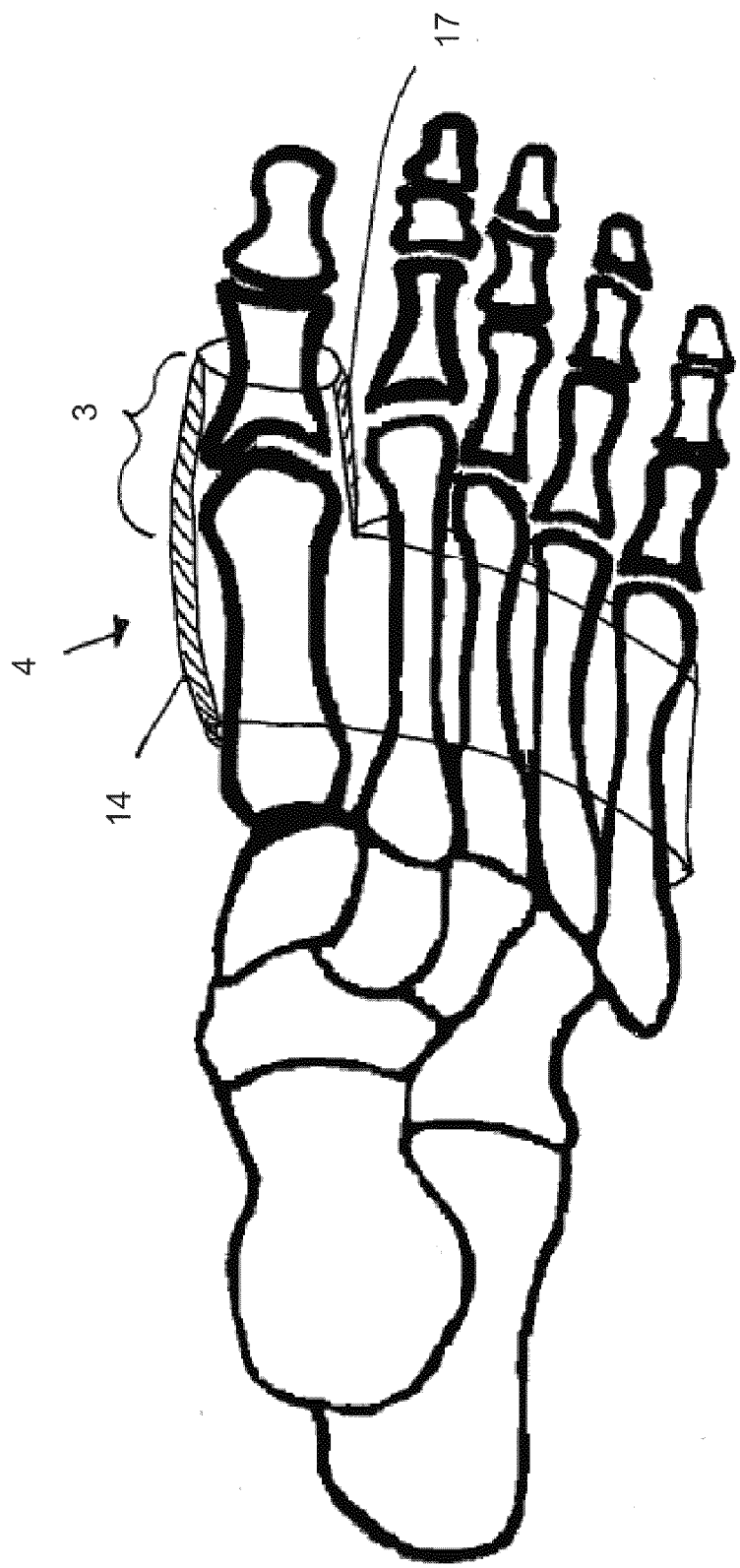
FIG. 5 also illustrates one example of a brace as worn, and certain elements thereof; wherein the stabilization members of the exemplary brace are illustrated.

Referring to FIG. 5, one embodiment of a brace is illustrated wherein the distal portion 3 is adapted to encapsulate and span the length of a portion of the metatarsal bone, the entire metatarsophalangeal joint, and a portion of the proximal phalanx bone. As shown, the medial face 4 comprises a primary medial stabilization member 14 spanning the entire length of the medial face 4. Additionally, the brace comprises a primary inter-phalangeal stabilization member 17 spanning the entire length of the inter-phalangeal face 9. In some embodiments, the stabilization members 14, 17 have sufficient rigidity, resiliency, cushioning, or combinations thereof to support the metatarsophalangeal joint, reduce or maintain the intermetatarsal angle, enhance or maintain alignment of the hallux, or combinations thereof. In some embodiments, the stabilization members 14, 17 are respectively woven into the medial 4 and inter-phalangeal 9 faces. In some embodiments, one or more of the woven stabilization members 14, 17 are polyfluorocarbon fibers. In some embodiments, one or more of the woven stabilization members 14, 17 are carbon fibers.

In some embodiments, wherein one or more of the stabilization members 14, 17 are polyfluorocarbon, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein the stabilization members 14, 17 are carbon fibers, the brace is used to support the metatarsophalangeal joint, reduce or maintain the intermetatarsal angle, enhance or maintain alignment of the hallux, or combinations thereof in a subject having minor to severe hallux valgus.

Figure 6:
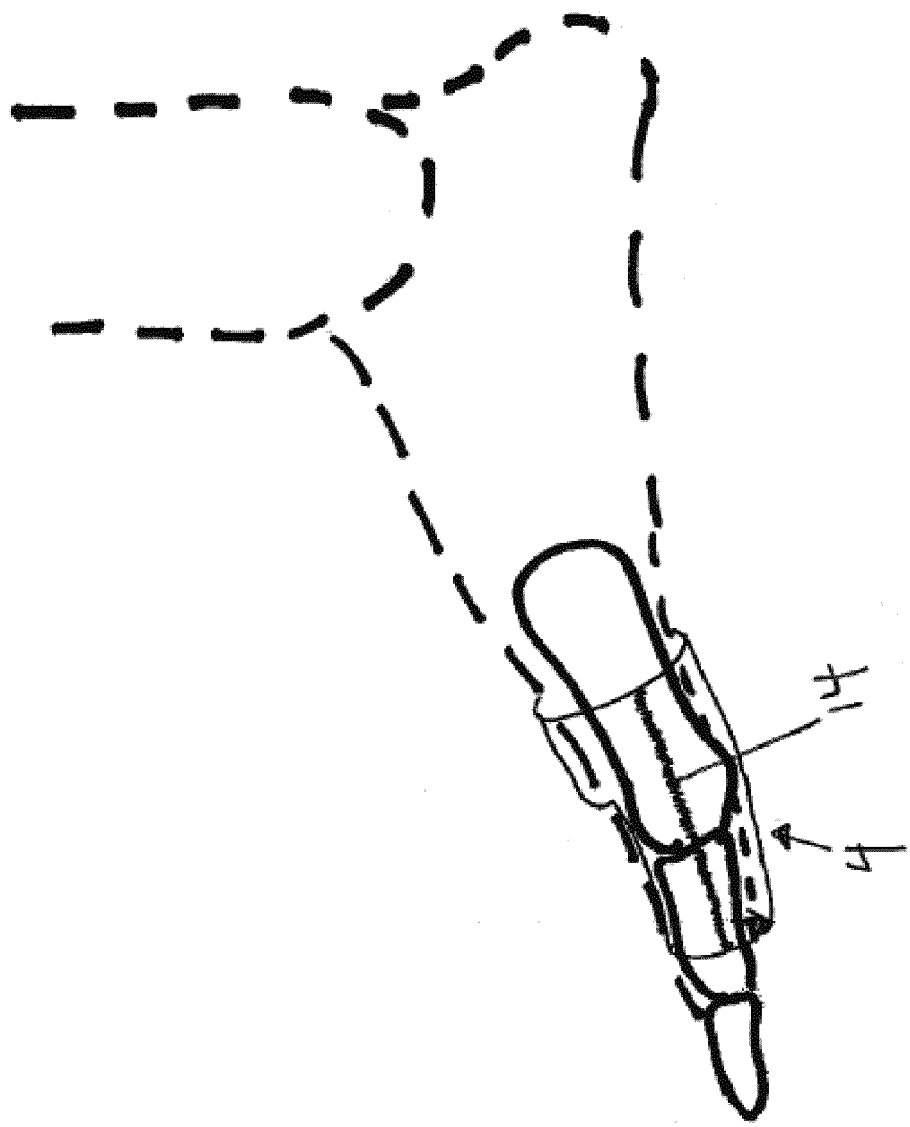
FIG. 6 illustrates an additional example of a brace as worn, as viewed from the medial position, and certain elements thereof; wherein the stabilization members of the exemplary brace are illustrated.

Referring to FIG. 6, one embodiment of a brace is illustrated wherein the distal portion (not labeled) is adapted to encapsulate and span at least the length of a portion of the proximal phalanx bone; and wherein the primary medial stabilization member 14 is stitching. In some embodiments, the stitching may be of polyfluorocarbon fibers. In some embodiments, the stitching may be of carbon fibers.

Figure 7:
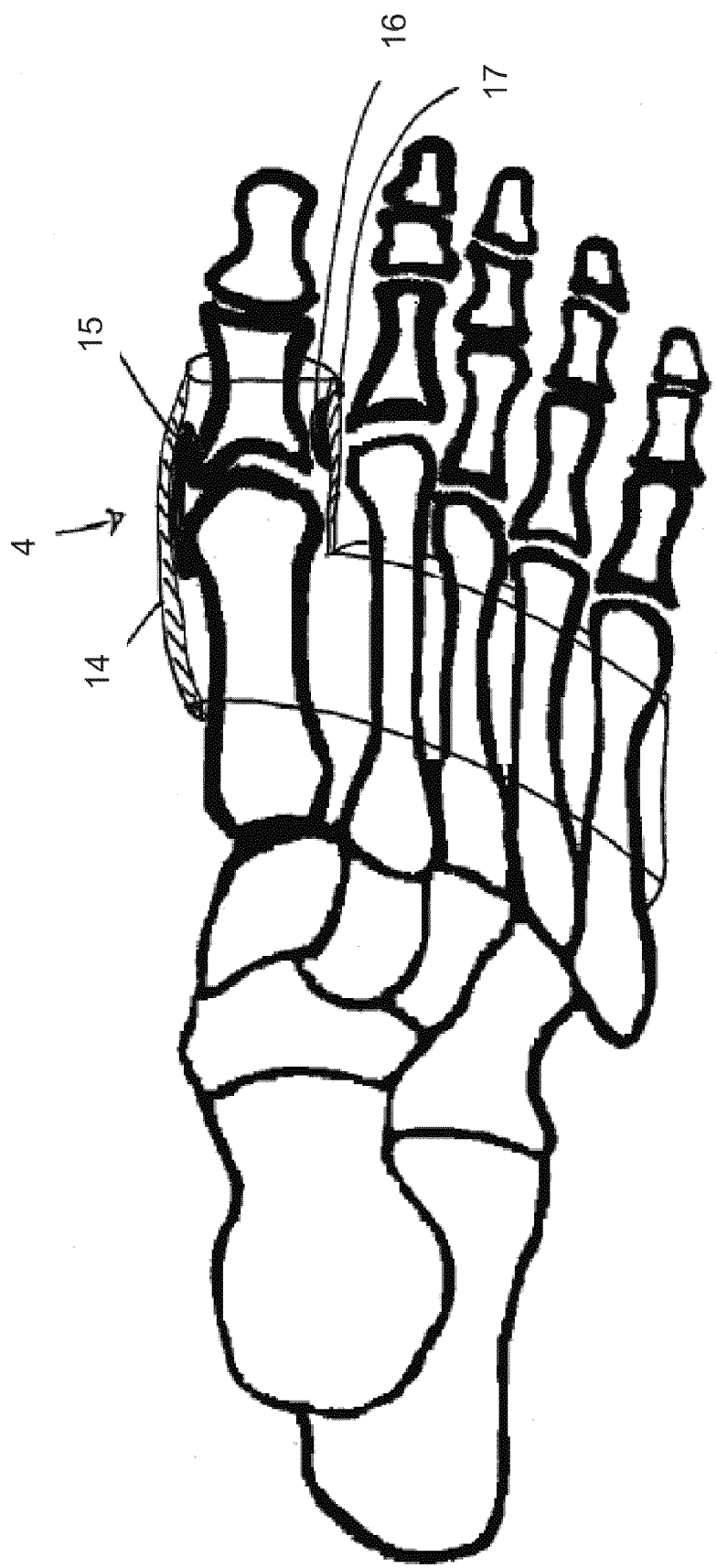
FIG. 7 illustrates one example of a brace as worn, and certain elements thereof; wherein the stabilization members of the exemplary brace are illustrated.

Referring to FIG. 7, one embodiment of a brace is illustrated wherein the distal portion (not labeled) is adapted to encapsulate and span the length of a portion of the metatarsal bone, the entire metatarsophalangeal joint, and a portion of the proximal phalanx bone. As shown, the medial face 4 comprises a primary medial stabilization member 14 spanning the entire length of the medial face 4 and a secondary medial stabilization member 15 spanning a portion of the length of the medial face 4. Additionally, the brace comprises a primary inter-phalangeal stabilization member 17 spanning the entire length of the inter-phalangeal face 9 and a secondary inter-phalangeal stabilization member 16 spanning a portion of the length of the inter-phalangeal face 9. In some embodiments, the stabilization members 14-17 have sufficient rigidity, resiliency, cushioning, or combination thereof to support the metatarsophalangeal joint, reduce or maintain the intermetatarsal angle, enhance or maintain alignment of the hallux, or combinations thereof. In some embodiments, the primary stabilization members 14, 17 are respectively woven into the medial 4 and inter-phalangeal (not labeled) faces. In some embodiments, one or more of the woven stabilization members 14, 17 are polyfluorocarbon. In some embodiments, one or more of the woven stabilization members 14, 17 are carbon fibers. In some embodiments, the secondary stabilization members 15, 16 are interior-oriented pads, inserts, or cushions. In some embodiments, the secondary stabilization members 15, 16 are hydrogels.

In some embodiments, wherein one or more of the primary stabilization members 14, 17 is a polyfluorocarbon and one or more of the secondary stabilization members 15, 16 is a hydrogel, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein one or more of the primary stabilization members 14, 17 comprise carbon fibers and one or more of the secondary stabilization members 15, 16 comprise a hydrogel, the brace is used to support the metatarsophalangeal joint, reduce or maintain the intermetatarsal angle, enhance or maintain alignment of the hallux, or combinations thereof in a subject having minor to severe hallux valgus.

Figure 8:
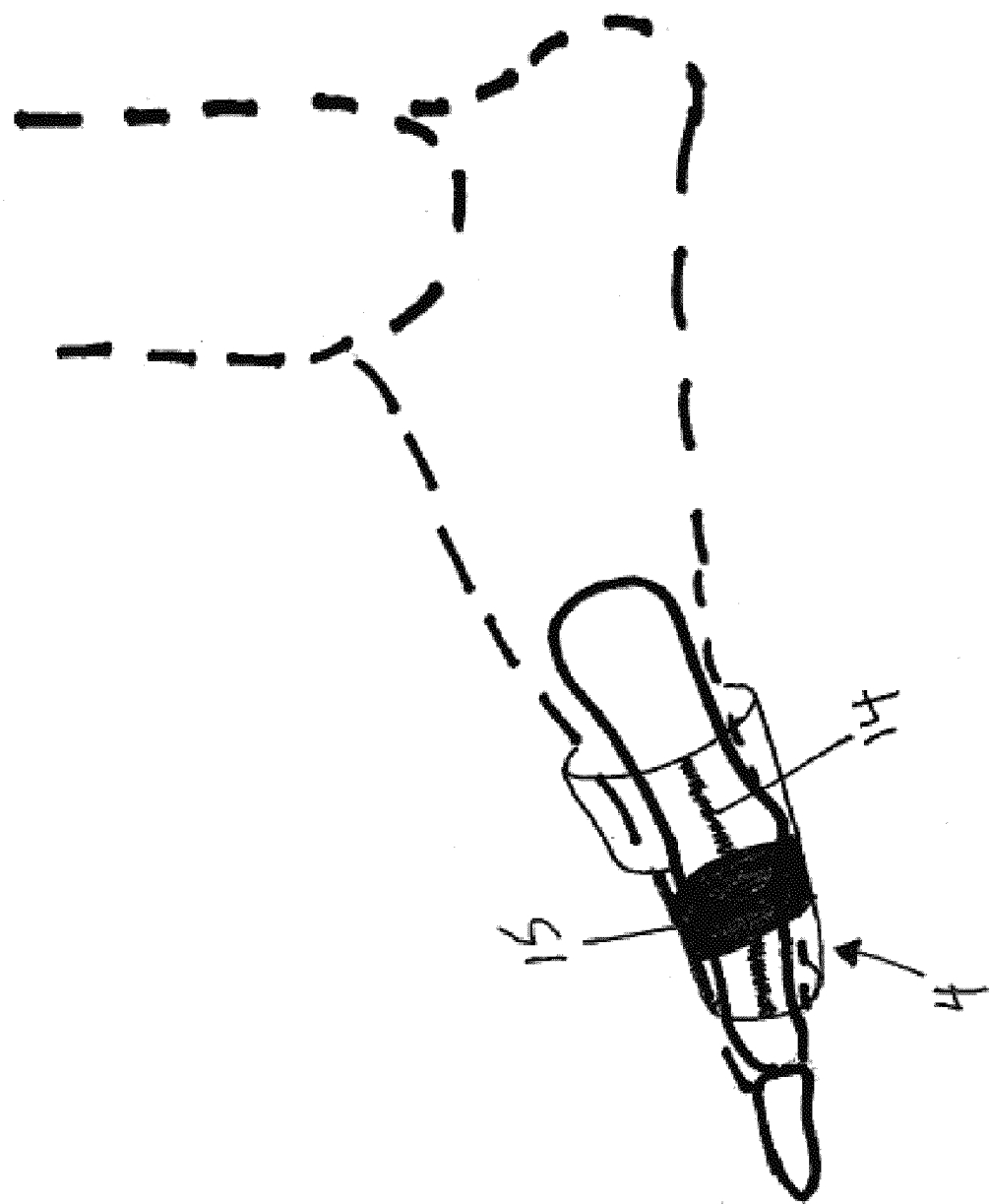
FIG. 8 illustrates an additional example of a brace as worn, as viewed from the medial position, and certain elements thereof; wherein the stabilization members of the exemplary brace are illustrated.

Referring to FIG. 8, one embodiment of a brace is illustrated wherein the primary medial stabilization member 14 is stitching and the secondary medial stabilization member 15 is a hydrogel. In some embodiments, the stitching may be of polyfluorocarbon fibers. In some embodiments, the stitching may be of carbon fibers. In some embodiments, the hydrogel may be selected from polyHEMA and silicone hydrogels.

Figure 9:
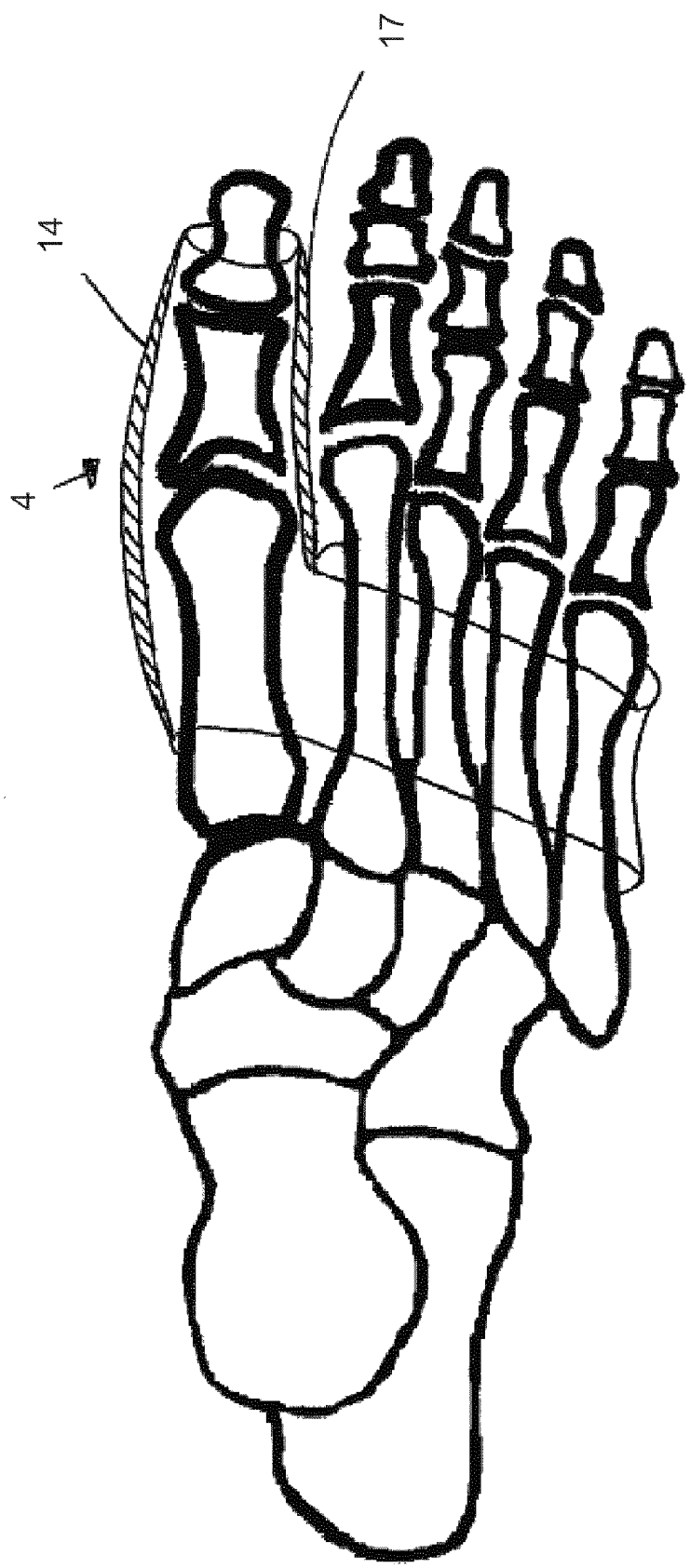
FIG. 9 also illustrates an example of a brace as worn, and certain elements thereof; wherein the stabilization members of the exemplary brace are illustrated.

Referring to FIG. 9, one embodiment of a brace is illustrated wherein the distal portion (not labeled) is adapted to encapsulate and span the length of a portion of the metatarsophalangeal joint, the entire proximal phalanx bone, and a portion of the distal phalanx bone. As shown, the medial face 4 comprises a primary medial stabilization member 14 spanning the entire length of the medial face 4. Additionally, the brace comprises a primary inter-phalangeal stabilization member 17 spanning the entire length of the inter-phalangeal face (not labeled). In some embodiments, the stabilization members 14, 17 have sufficient rigidity, resiliency, cushioning, or combinations thereof to support the metatarsophalangeal joint, reduce or maintain the intermetatarsal angle, enhance or maintain alignment of the hallux, or combinations thereof. In some embodiments, the stabilization members 14, 17 are respectively woven into the medial 4 and inter-phalangeal 9 faces. In some embodiments, one or more of the woven stabilization members 14, 17 are polyfluorocarbon fibers. In some embodiments, one or more of the woven stabilization members 14, 17 are carbon fibers.

In some embodiments, wherein one or more of the stabilization members 14, 17 are polyfluorocarbon, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein the stabilization members 14, 17 are carbon fibers, the brace is used to support the metatarsophalangeal joint, reduce or maintain the intermetatarsal angle, enhance or maintain alignment of the hallux, or combinations thereof in a subject having minor to severe hallux valgus.

Figure 10:
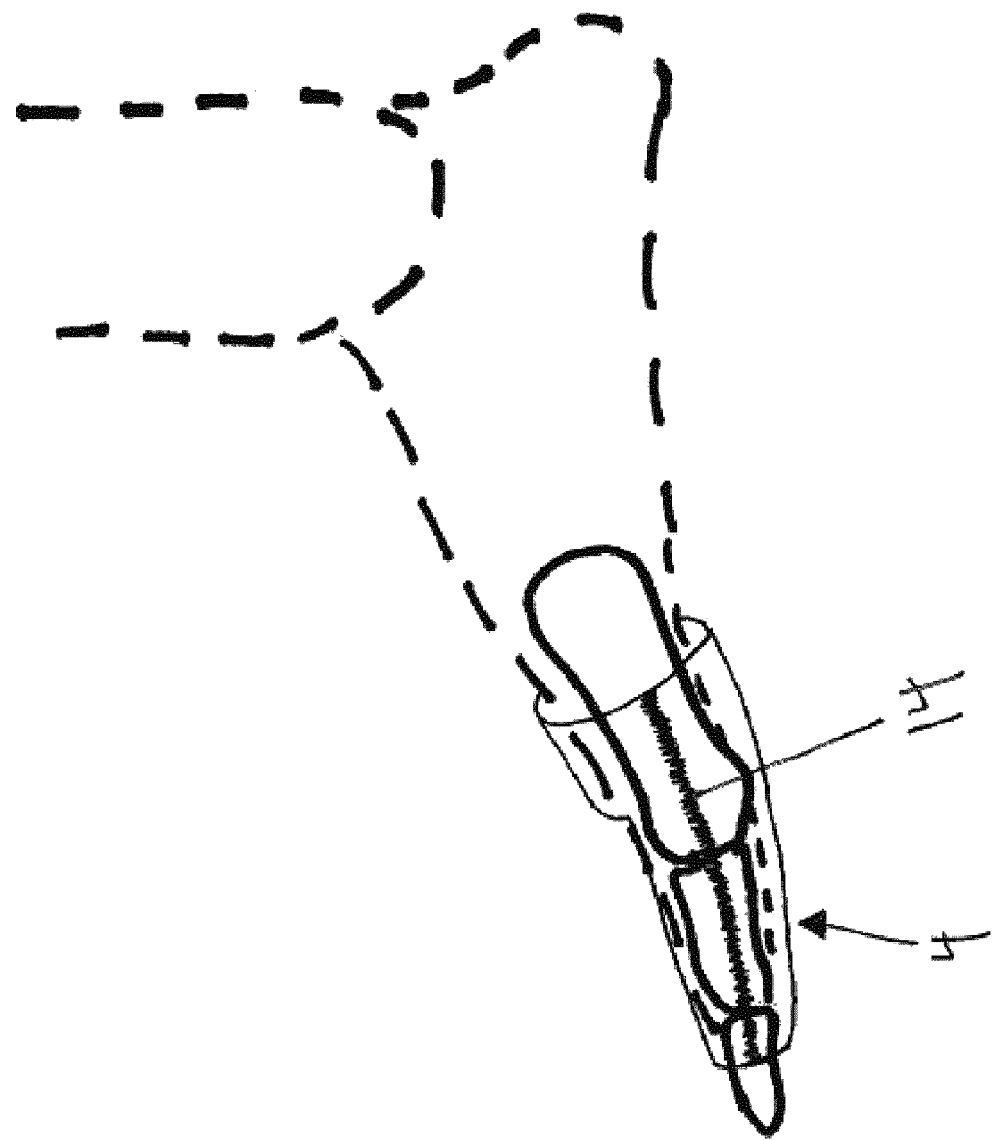
FIG. 10 illustrates an another example of a brace as worn, as viewed from the medial position, and certain elements thereof; wherein the stabilization members of the exemplary brace are illustrated.

Referring to FIG. 10, one embodiment of a brace is illustrated wherein the distal portion (not labeled) is adapted to encapsulate and span the length of at least a portion of the distal phalanx bone and wherein the primary medial stabilization member 14 is stitching. In some embodiments, the stitching may be of polyfluorocarbon fibers. In some embodiments, the stitching may be of carbon fibers.

Figure 11:
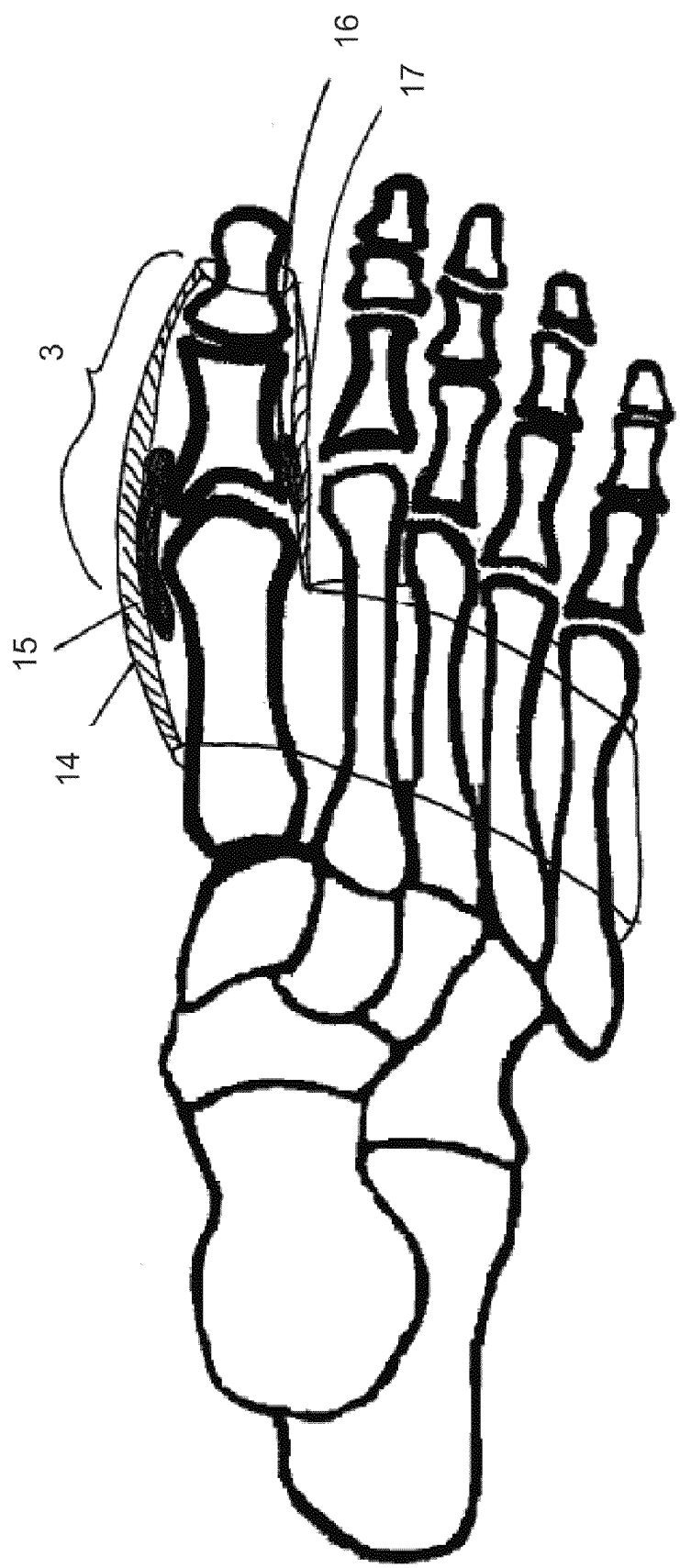
FIG. 11 illustrates one example of a brace as worn, and certain elements thereof; wherein the stabilization members of the exemplary brace are illustrated.

Referring to FIG. 11, one embodiment of a brace is illustrated wherein the distal portion 3 is adapted to encapsulate and span the length of a portion of the metatarsophalangeal joint, the entire proximal phalanx bone, and a portion of the distal phalanx bone. As shown, the medial face 4 comprises a primary medial stabilization member 14 spanning the entire length of the medial face 4 and a secondary medial stabilization member 15 spanning a portion of the length of the medial face 4. Additionally, the brace comprises a primary interphalangeal stabilization member 17 spanning the entire length of the inter-phalangeal face (not labeled) and a secondary inter-phalangeal stabilization member 16 spanning a portion of the length of the inter-phalangeal face. In some embodiments, the stabilization members 14-17 have sufficient rigidity, resiliency, cushioning, or combinations thereof to support the metatarsophalangeal joint, reduce or maintain the intermetatarsal angle, enhance or maintain alignment of the hallux, or combinations thereof. In some embodiments, the primary stabilization members 14, 17 are respectively woven into the medial 4 and inter-phalangeal faces. In some embodiments, one or more of the woven stabilization members 14, 17 are polyfluorocarbon fibers. In some embodiments, one or more of the woven stabilization members 14, 17 are carbon fibers. In some embodiments, the secondary stabilization members 15, 16 are interior-oriented pads, inserts, or cushions. In some embodiments, the secondary stabilization members 15, 16 are hydrogels.

In some embodiments, wherein one or more of the primary stabilization members 14, 17 is a polyfluorocarbon and one or more of the secondary stabilization members 15, 16 is a hydrogel, the brace is used to support the metatarsophalangeal joint, reduce or maintain the intermetatarsal angle, enhance or maintain alignment of the hallux, or combinations thereof in a subject having minor to moderate hallux valgus. In some embodiments, wherein one or more of the primary stabilization members 14, 17 is carbon fibers and one or more of the secondary stabilization members 15, 16 is a hydrogel, the brace is used to support the metatarsophalangeal joint, reduce or maintain the intermetatarsal angle, enhance or maintain alignment of the hallux, or combinations thereof in a subject having minor to severe hallux valgus.

Figure 12:
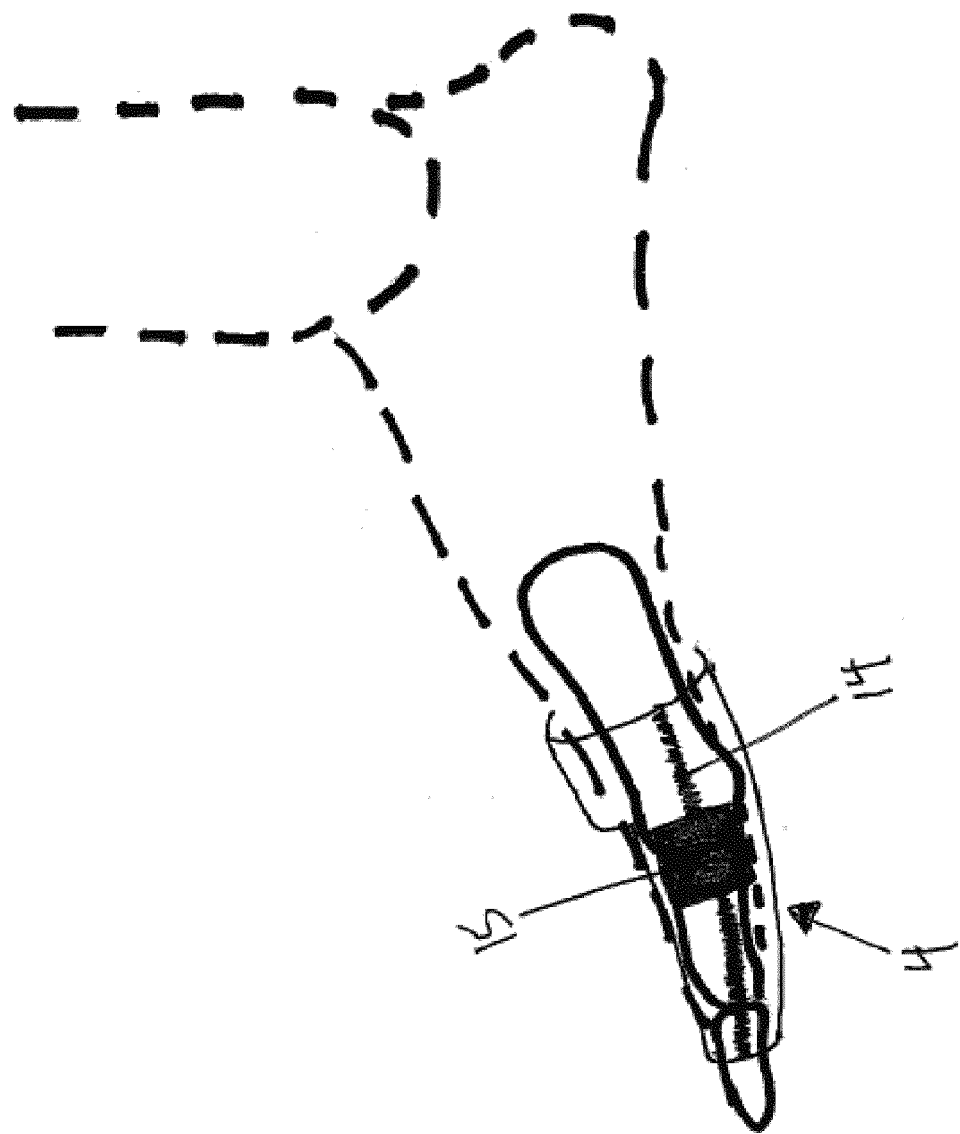
FIG. 12 additionally illustrates an example of a brace as worn, as viewed from the medial position, and certain elements thereof; wherein the stabilization members of the exemplary brace are illustrated.

Referring to FIG. 12, one embodiment of a brace is illustrated wherein the distal portion (not labeled) is adapted to encapsulate and span the length of at least a portion of the distal phalanx bone; wherein the primary medial stabilization member 14 is stitching; and wherein the secondary medial stabilization member 15 is hydrogel. In some embodiments, the stitching may be of polyfluorocarbon fibers. In some embodiments, the hydrogel may be selected from poly-HEMA and silicone hydrogels.

In various embodiments, a provided brace may be used in combination with a provided toe brace to support the metatarsophalangeal joint, reduce or maintain the intermetatarsal angle, enhance or maintain alignment of the hallux, or combinations thereof in a subject having hallux valgus. In some embodiments, a provided toe brace may be used without a brace.

In various embodiments, toe braces for treating hallux valgus in the foot of a subject are provided, comprising a first member comprising opposing longitudinal edges, each edge having one or more locking members; a second member comprising opposing longitudinal edges, each edge having one or more cavities adapted to receive the one or more locking members; wherein the one or more locking members and one or more cavities are adapted to reversibly lock the first member to the second member; and wherein the reversibly locked first member and second member define a cavity adapted to receive at least a portion of the hallux.

Figure 13:
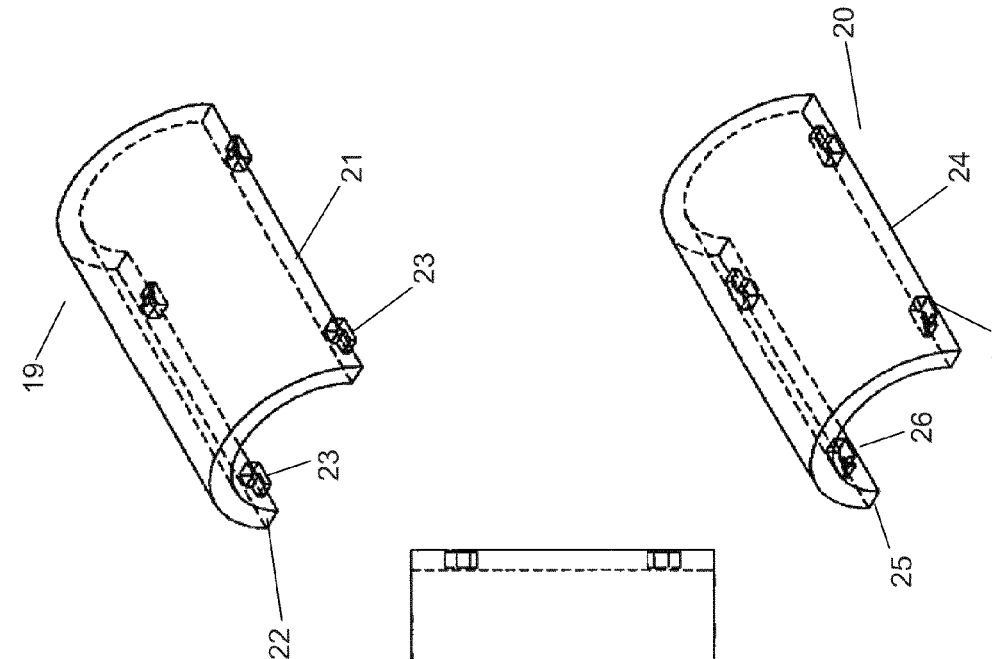
FIGS. 13-15 illustrate an example of a toe brace and elements thereof.
Figure 13:
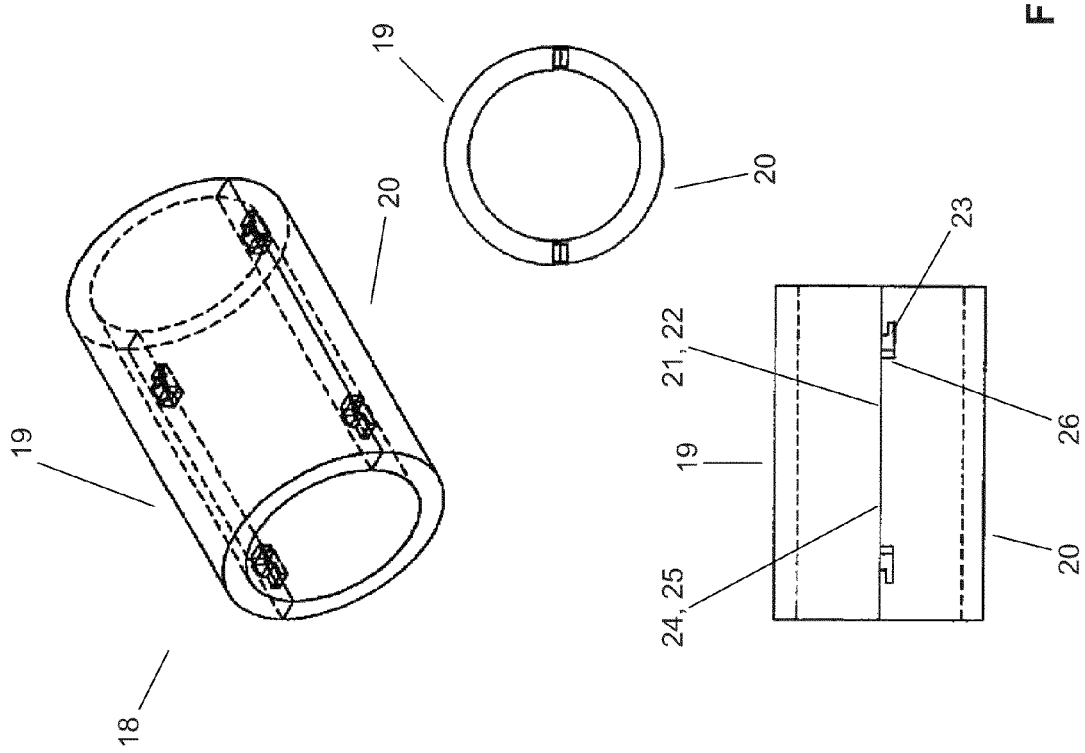
Figure 14:
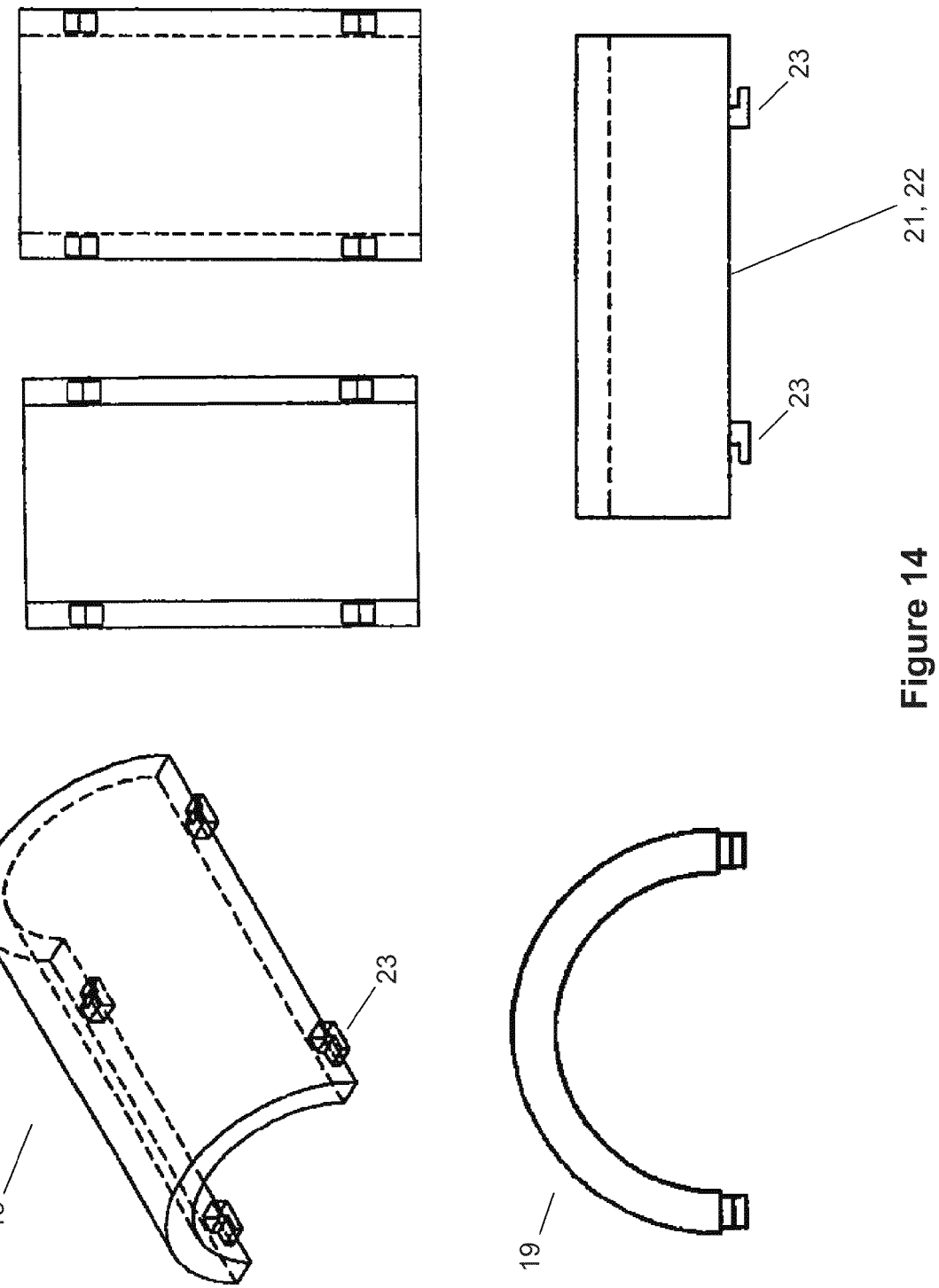
Figure 15:
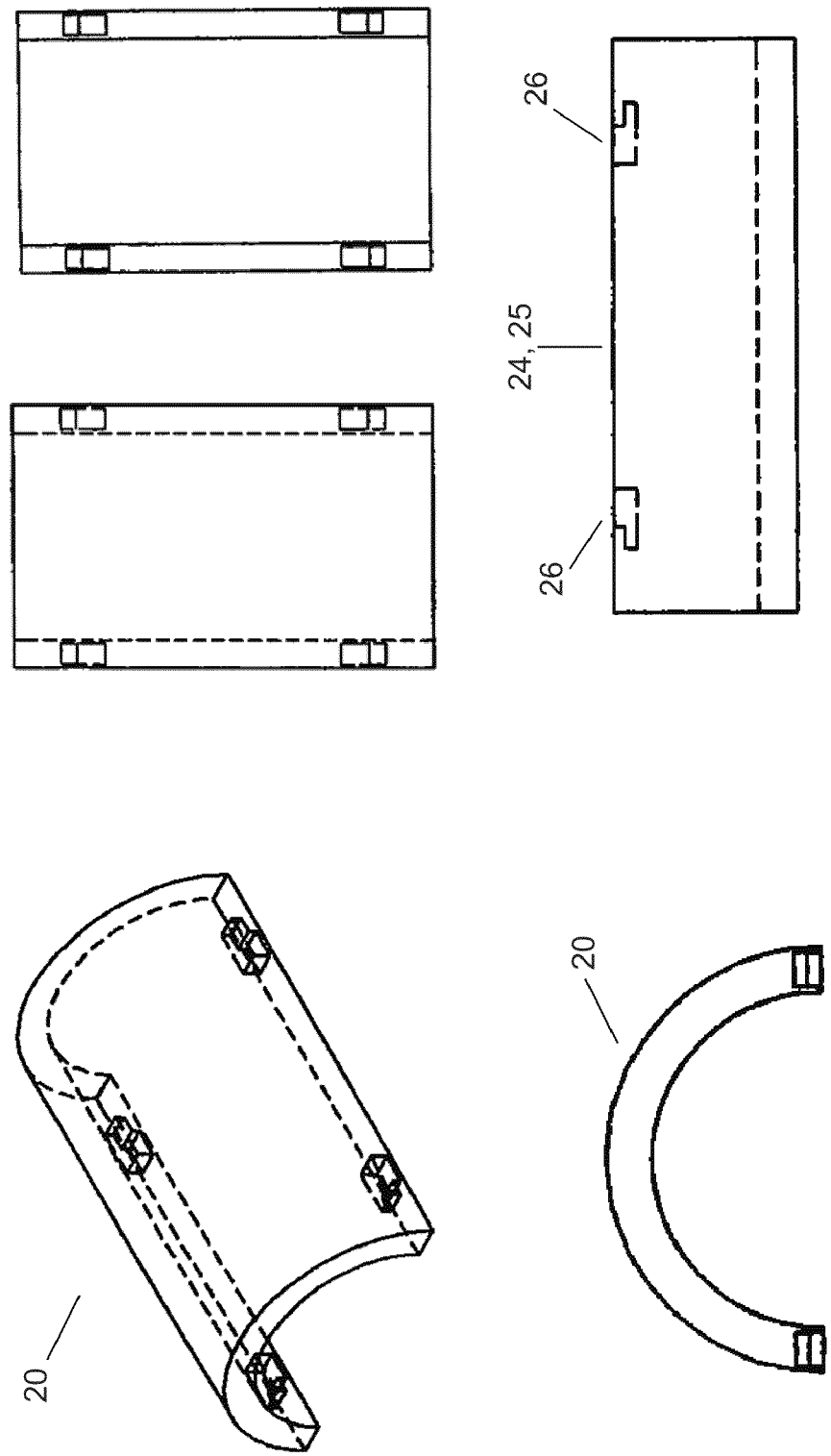
Figure 16:
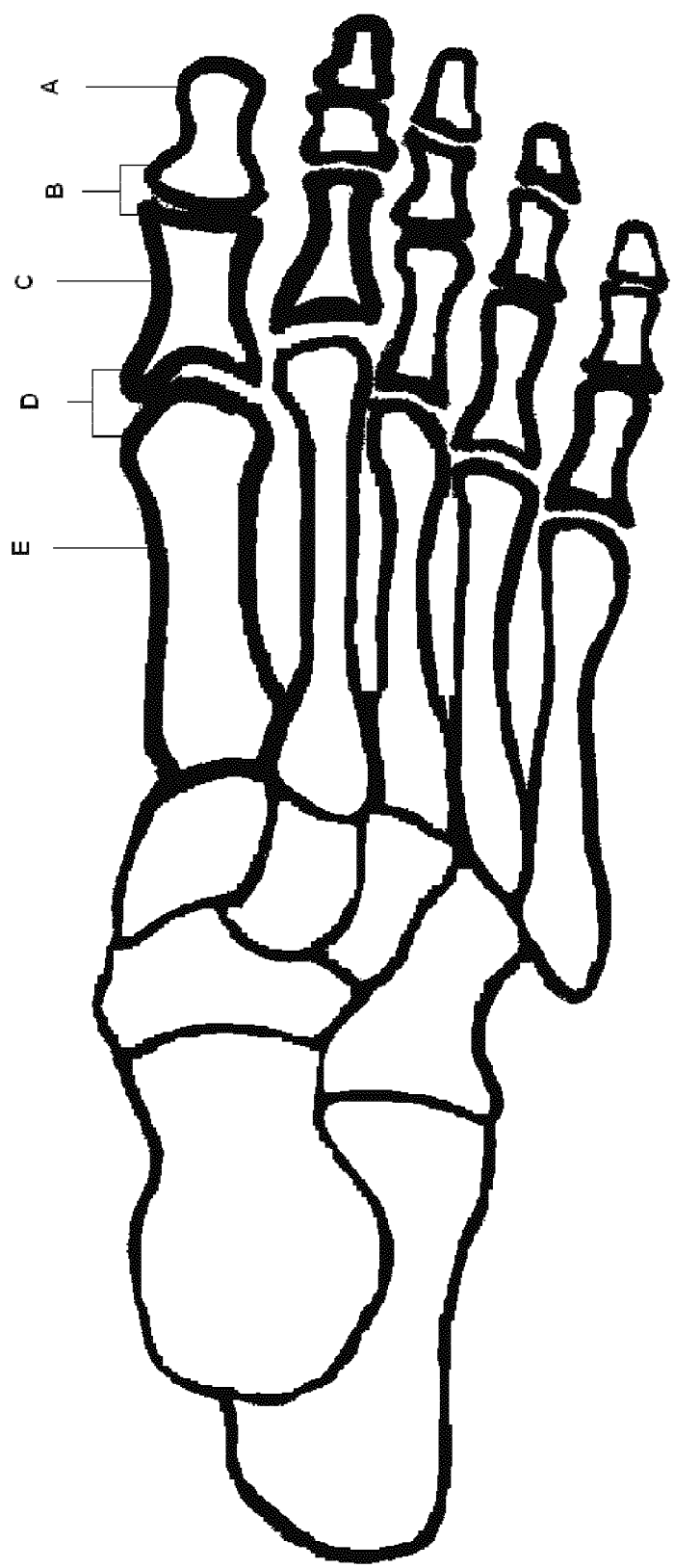
FIG. 16 illustrates the bones of the foot, including those most relevant to hallux valgus: A, distal phalanx; B, interphalangeal joint; C, proximal phalanx; D, metatarsophalangeal joint; E, metatarsal.
Figure 17:
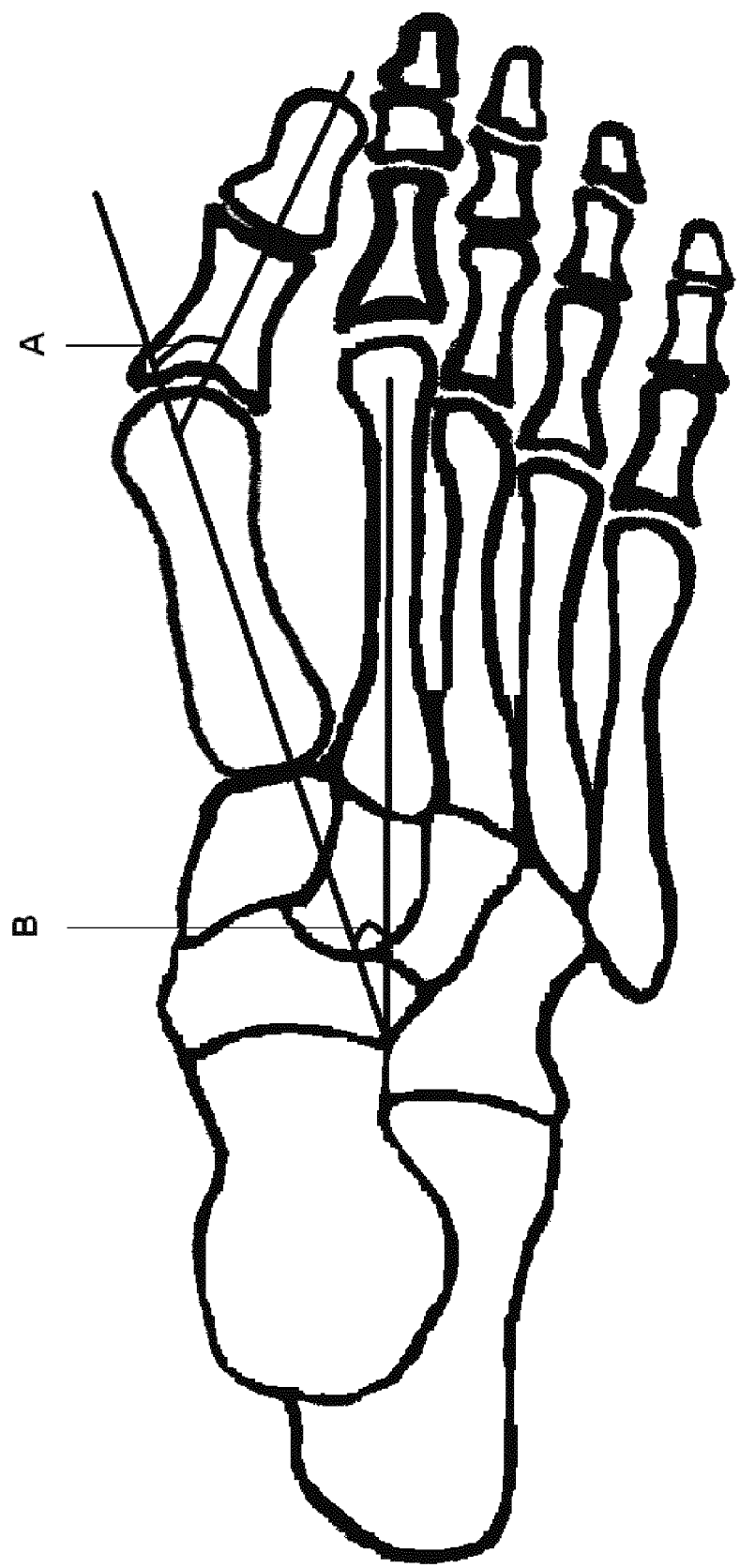
FIG. 17 illustrates deformity of the A, hallux valgus angle; and B, intermetatarsal angle.

Referring to FIGS. 13-15, embodiments of toe braces are illustrated. As illustrated, a toe brace 18 comprises a ventral member 19 and a dorsal member 20. As shown, when joined the members 19, 20 have a cylindrical shape and when not joined, each is a semi-cylinder having semi-circular cross-section. However, it is contemplated that one or both members 19, 20 could have an alternative cross-section. Accordingly, it is also contemplated that the joined members may have a non-cylindrical shape. For example, the shape may be conical or tapered.

As shown, the ventral member 19 comprises opposing longitudinal edges 21, 22, each with at least one locking member 23. As shown, the ventral member 19 comprises four locking members 23, each being a flange member. The locking members 23 are adapted to reversibly lock the ventral member 19 to the dorsal member 20. It is also contemplated that alternative locking means and alternative numbers and configurations of locking members may be utilized.

As shown, the dorsal member 20 comprises opposing longitudinal edges 24, 25, each with at least one cavity 26, wherein each cavity 26 is adapted to receive a corresponding locking member 23. As shown, the dorsal member 20 comprises four cavities 26.

With the locking members 23 and cavities 26 shown, reversible locking of the ventral member 19 to the dorsal member 20 is achieved by aligning the locking members 23 with the cavities 26 and either pressing or sliding the locking members 23 into the cavities 26. Unlocking is achieved by either pulling or sliding the locking members 23 out of the cavities 26.

It is contemplated that alternative configurations of the members of the toe brace are possible. For example, either or both of the ventral and dorsal members may independently comprise one or more locking members and one or more cavities. For example, the ventral member may comprise four cavities, and the dorsal member may comprise four locking members.

In some embodiments, toe brace may be selected from small, medium, or large sizes as necessary to approximate the anatomy of the subject. In some embodiments, toe brace may comprise one or more dimensions set forth in Table 3. In some embodiments, a toe brace may be customized to the anatomy of the subject. The provided braces may be comprised of any material suitable for use with wearable braces. For example, synthetic fibers (including but not limited to carbon fibers and polychloroprene rubber such as for example Neoprene™), polymeric materials [including but not limited to ultra-high molecular weight polyethylene, polypropylene, PEEK, and fluorocarbon polymers such as, for example, Teflon®], and combinations thereof may be a suitable materials.

TABLE 3

| Measurement | Dimension (mm) |
|---|---|
| Great Toe Circumference | 70-102 |
| Great Toe Length | 41-49 |

In various embodiments, methods of treating hallux valgus in a subject are provided and comprise applying to the subject foot one or both of (i) a toe brace, comprising a first member comprising opposing longitudinal edges, each edge having one or more locking members; a second member comprising opposing longitudinal edges, each edge having one or more cavities adapted to receive the one or more locking members; wherein the one or more locking members and one or more cavities are adapted to reversibly lock the first member to the second member; and wherein the reversibly locked first member and second member define a cavity adapted to receive at least a portion of the hallux of the foot; and (ii) a brace, comprising a distal portion comprising a cavity adapted to receive at least a portion of the hallux; a proximal portion comprising a cavity adapted to receive at least a portion of the midfoot and hallux; and one or more stabilization members adapted to provide one or more of rigidity, resiliency, or cushioning to at least a part of the distal portion, at least a part of the proximal portion, or combinations thereof; wherein the applied braces support the metatarsophalangeal joint of the foot, reduce or maintain the intermetatarsal angle of the foot, enhance or maintain alignment of the hallux, or combinations thereof.

What is claimed is:

1. A toe brace for treating hallux valgus in the foot of a subject, comprising:
   a first member comprising opposing longitudinal edges, each edge having one or more locking members;
   a second member comprising opposing longitudinal edges, each edge having one or more cavities adapted to receive the one or more locking members;
   wherein the one or more locking members and one or more cavities are adapted to reversibly lock the first member to the second member; and
   wherein the reversibly locked first member and second member define a cavity adapted to receive at least a portion of the hallux.

2. A brace according to claim 1, wherein the first member and second members are adapted to support the metatarsophalangeal joint of the foot, reduce or maintain the intermetatarsal angle of the foot, enhance or maintain alignment of the hallux, or combinations thereof.

3. A toe brace according to claim 1, wherein the reversibly locked first member and second member have a shape selected from cylindrical, conical, or tapered.

4. A toe brace according to claim 1, wherein the one or more locking members are flanges.

5. A method of treating hallux valgus in a subject, comprising:
   applying to the subject foot one or both of:
      (i) a toe brace, comprising:
         a first member comprising opposing longitudinal edges, each edge having one or more locking members;
         a second member comprising opposing longitudinal edges, each edge having one or more cavities adapted to receive the one or more locking members;
         wherein the one or more locking members and one or more cavities are adapted to reversibly lock the first member to the second member; and
         wherein the reversibly locked first member and second member define a cavity adapted to receive at least a portion of the hallux of the foot; and
      (ii) a foot brace, comprising:
         a distal portion comprising a cavity adapted to receive at least a portion of the hallux;
         a proximal portion comprising a cavity adapted to receive at least a portion of the midfoot and hallux; and
         one or more stabilization members adapted to provide one or more of rigidity, resiliency, or cushioning to at least a part of the distal portion, at least a part of the proximal portion, or combinations thereof;
      wherein the applied braces support the metatarsophalangeal joint of the foot, reduce or maintain the intermetatarsal angle of the foot, enhance or maintain alignment of the hallux, or combinations thereof.

6. A method according to claim 5, wherein the reversibly locked first member and second member of the toe brace has a shape selected from cylindrical, conical, or tapered.

7. A method according to claim 5, wherein the one or more locking members of the toe brace are flanges.

8. A method according to claim 5, wherein the one or more stabilization members of the foot brace are independently selected from woven fibers, stitching, panels, pads, rods, ribs, cushions, and inserts.

9. A method according to claim 8, wherein the one or more stabilization members of the foot brace are selected from natural fibers, synthetic fibers, polymeric materials, hydrogels, and combinations thereof.

10. A method according to claim 5, wherein the distal portion of the foot brace encapsulates at least a portion of the hallux of the foot and spans a length of at least a portion of the proximal phalanx bone of the foot.

11. A method according to claim 10, wherein the proximal portion of the foot brace is continuous with the distal portion.

12. A method according to claim 11, wherein the foot brace comprises a medial face defined by portions of the distal and proximal portions, the medial face spanning a length of at least a portion of the metatarsal and proximal phalanx on the medial side of the hallux of the foot.

13. A method according to claim 12, wherein at least one of the stabilization members of the foot brace is a primary stabilization member integral with at least a portion of the medial face, said primary stabilization member selected from woven fibers, stitching, a panel, a rod, and a rib.

14. A method according to claim 13, wherein the primary stabilization member is selected from carbon fibers, Teflon, ultra-high molecular weight polyethylene, polyHEMA, silicon hydrogels, and combinations thereof.

15. A method according to claim 12, wherein the distal portion cavity of the foot brace is defined by (i) a distal face and an inter-phalangeal face of the distal portion, (ii) the portion of the medial face defined by the distal portion, and (iii) portions of ventral and dorsal faces that are defined by the distal portion, the ventral and dorsal faces being defined by portions of the distal and proximal portions.

16. A method according to claim 15, wherein the proximal portion cavity of the foot brace is defined by (i) a proximal face, a lateral face, and an intermediate face of the proximal portion, (ii) the portion of the medial face defined by the proximal portion, and (iii) portions of the ventral and dorsal faces that are defined by the proximal portion.

17. A method according to claim 16, wherein the inter-phalangeal face is adapted to span the length of at least a portion of the proximal phalanx on the lateral side of the hallux.

18. A method according to claim 17, wherein the medial face and inter-phalangeal face span the length of at least a portion of the distal phalanx of the hallux.

19. A method according the claim 16, wherein the distal portion and proximal portion of the foot brace comprise a material of construction selected from rubber, synthetic rubber, natural fibers, and synthetic fibers.

20. A method according to claim 19, wherein the material of construction is Neoprene.

* * * * *